United States Patent
Gronke et al.

(10) Patent No.: US 11,318,207 B2
(45) Date of Patent: May 3, 2022

(54) PEGYLATION METHOD

(71) Applicant: BIOGEN MA INC., Cambridge, MA (US)

(72) Inventors: Robert S. Gronke, Boston, MA (US); Orlando A. Jaquez, Melrose, MA (US)

(73) Assignee: BIOGEN MA INC., Cambridge, MA (US)

( * ) Notice: Subject to any disclaimer, the term of this patent is extended or adjusted under 35 U.S.C. 154(b) by 713 days.

(21) Appl. No.: 15/504,379

(22) PCT Filed: Aug. 18, 2015

(86) PCT No.: PCT/US2015/045678
§ 371 (c)(1),
(2) Date: Feb. 16, 2017

(87) PCT Pub. No.: WO2017/030563
PCT Pub. Date: Feb. 23, 2017

(65) Prior Publication Data
US 2017/0232111 A1 Aug. 17, 2017

Related U.S. Application Data

(60) Provisional application No. 61/997,000, filed on Aug. 19, 2014.

(51) Int. Cl.
*A61K 47/60* (2017.01)
*C07K 14/565* (2006.01)

(52) U.S. Cl.
CPC ............ *A61K 47/60* (2017.08); *C07K 14/565* (2013.01)

(58) Field of Classification Search
None
See application file for complete search history.

(56) References Cited

U.S. PATENT DOCUMENTS

| | | |
|---|---|---|
| 2004/0043002 A1 | 3/2004 | El-Tayar et al. |
| 2004/0180054 A1 | 9/2004 | Kim |
| 2006/0100144 A1* | 5/2006 | Lang ...................... A61K 47/60 514/8.7 |
| 2009/0082537 A1 | 3/2009 | Ramon Hernandez et al. |
| 2012/0128629 A1 | 5/2012 | Roberts et al. |
| 2012/0258926 A1* | 10/2012 | Antochshuk ......... A61K 9/0019 514/43 |

FOREIGN PATENT DOCUMENTS

| | | |
|---|---|---|
| CN | 103113466 A | 5/2013 |
| CN | 103936847 A | 7/2014 |
| TW | 200619386 A | 6/2006 |
| WO | 03/061577 A2 | 7/2003 |
| WO | 2010131015 A1 | 11/2010 |
| WO | 2011122923 A2 | 10/2011 |
| WO | 2012055205 A1 | 5/2012 |
| WO | 2014/130811 A1 | 8/2014 |

OTHER PUBLICATIONS

Kim et al. J. Org. Chem. 50(11):1927-1931 (Year: 1985).*
Hu et al., 2005, Biochem. J., vol. 392, pp. 555-564 (Year: 2005).*
Baker, D. et al. "N-Terminally PEGylated Human lnterferon-β-1a with Improved Pharmacokinetic Properties and in Vivo Efficacy in a Melanoma Angiogenesis Model" Bioconjugate Chemistry, 2006, pp. 179-188, vol. 17, No. 1.
Basu, A. et al. "Structure-Function Engineering of lnterferon-β-1b for Improving Stability, Solubility, Potency, Immunogenicity, and Pharmacokinetic Properties by Site-Selective Mono-PEGylation" Bioconjugate Chemistry, 2006, pp. 618-630, vol. 17, No. 3.
International Search Report and Written Opinion issued in PCT/US2015/045678 dated Feb. 3, 2016 (14 pages).
Communication pursuant to Article 94(3) EPC cited in European Application No. 15 763 443.7 dated Apr. 24, 2018, 6 pages.
Office Action No. 6690 dated Jul. 25, 2019 in Colombian Application No. NC2017/0002512 with an English language translation, 12 pages.
Intention to Grant in European Application No. 15 763 443.7, dated Sep. 13, 2019, 6 pages.
Extended European Search Report cited in EP application 20180909.2 dated Jan. 25, 2021, 8 pages.

* cited by examiner

*Primary Examiner* — Gary B Nickol
*Assistant Examiner* — Jegatheesan Seharaseyon
(74) *Attorney, Agent, or Firm* — Rothwell, Figg, Ernst & Manbeck, P.C.

(57) ABSTRACT

The present invention relates to a method for PEGylating interferon beta.

37 Claims, 1 Drawing Sheet

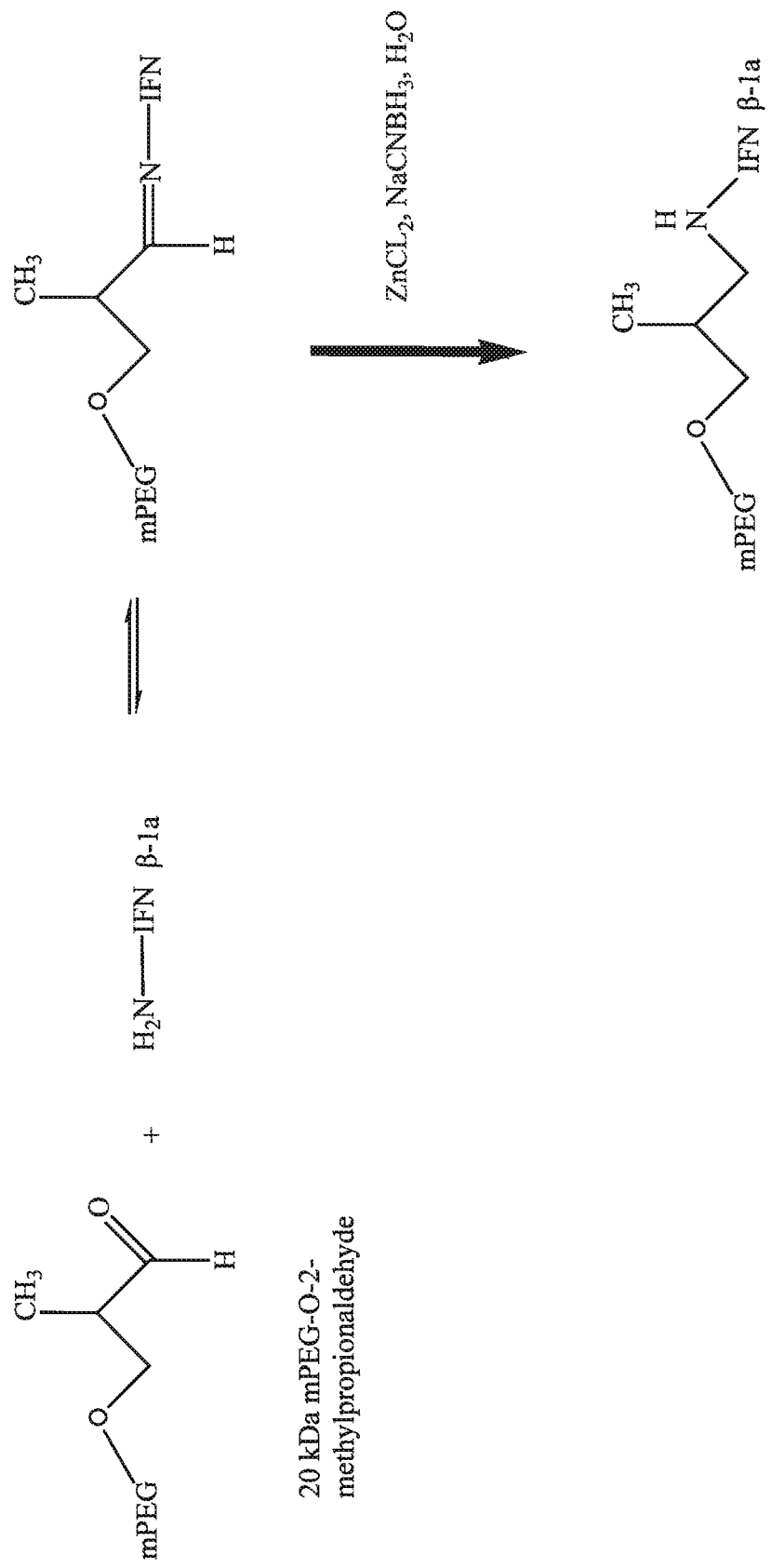

PEGYLATION METHOD

CROSS-REFERENCE TO RELATED APPLICATIONS

The present application is a national stage filing under 35 U.S.C. § 371 of PCT/US/2015/45678, filed on 18 Aug. 2015, which in turn claims the benefit of priority to and the benefit of U.S. Provisional Application No. 61/997,000, filed 19 Aug. 2014. Each application is incorporated herein by reference in its entirety.

FIELD OF THE INVENTION

The present invention relates to a method for PEGylating interferon beta.

BACKGROUND OF THE INVENTION

Covalent attachment of hydrophilic polymers, such as polyalkylene glycol polymers, also known as polyalkylene oxides, to biologically-active molecules and surfaces is of interest in biotechnology and medicine. In particular, much research has focused on the use of poly(ethylene glycol) (PEG), also known as or poly(ethylene oxide) (PEO), conjugates to enhance solubility and stability and to prolong the blood circulation half-life and exposure of biological molecules, including for example, interferon beta.

In its most common form, PEG is a linear polymer terminated at each end with hydroxyl groups: $HO-CH_2CH_2O-(CH_2CH_2O)_n-CH_2CH_2-OH$. This polymer, alpha-, omega-dihydroxylpoly(ethylene glycol), can also be represented as HO-PEG-OH, where it is understood that the -PEG- symbol represents the following structural unit: $CH_2CH_2O-(CH_2CH_2O)_n-CH_2CH_2-$ where n typically ranges from about 4 to about 10,000. PEG is commonly used as methoxy-PEG-OH, or mPEG, in which one terminus contains the relatively inert methoxy group, while the other terminus is a hydroxyl group that is subject to ready chemical modification. Additionally, random or block copolymers of different alkylene oxides (e.g., ethylene oxide and propylene oxide) that are closely related to PEG in their chemistry can be substituted for PEG in many of its applications.

To couple PEG to a molecule of interest, it is often necessary to activate the PEG by preparing a derivative of the PEG having a reactive functional group on at least at one terminus. The functional group is chosen based on the type of available reactive group on the molecule that will be coupled to the PEG.

PEG is a polymer having the properties of solubility in water and in many organic solvents, lack of toxicity, and lack of immunogenicity. One use of PEG is to covalently attach the polymer to insoluble molecules to make the resulting PEG-molecule "conjugate" soluble. For example, it has been shown that the water-insoluble drug paclitaxel, when coupled to PEG, becomes water-soluble. Greenwald, et al., 1995, *J Org Chem* 60:331-336.

One factor limiting the usefulness of proteinaceous substances for medical treatment applications is that, when given parenterally, they are eliminated from the body within a short time. This elimination can occur as a result of degradation by proteases or by clearance using normal pathways for protein elimination such as by filtration in the kidneys. Oral administration of these substances is even more problematic because, in addition to proteolysis in the stomach, the high acidity of the stomach destroys these substances before they reach their intended target tissue. The problems associated with these routes of administration of proteins are well known in the pharmaceutical industry, and various strategies are being employed in attempts to solve them. A great deal of work dealing with protein stabilization has been published. Various ways of conjugating proteins with polymeric materials are known, including use of dextrans, polyvinyl pyrrolidones, glycopeptides, polyethylene glycol, and polyamino acids. The resulting conjugated polypeptides are reported to retain their biological activities and solubility in water for parenteral applications.

Of particular interest is maintaining the biological activity of interferons while reducing the toxicity involved with use of these proteins for treating human patients. Interferons are a family of naturally-occurring small proteins and glycoproteins produced and secreted by most nucleated cells in response to viral infection as well as to other antigenic stimuli. Interferons render cells resistant to viral infection and exhibit a wide variety of actions on cells. They exert their cellular activities by binding to specific membrane receptors on the cell surface. Once bound to the cell membrane, interferons initiate a complex sequence of intracellular events. In vitro studies have demonstrated that these include the induction of certain enzymes; suppression of cell proliferation, immunomodulation activities such as enhancement of the phagocytic activity of macrophages; augmentation of the specific cytotoxicity of lymphocytes for target cells; and inhibition of virus replication in virus-infected cells.

Interferons have been tested in the treatment of a variety of clinical disease states. The use of human interferon beta has been established in the treatment of multiple sclerosis. Two forms of recombinant interferon beta (IFN β), have recently been licensed in Europe and the U.S. for treatment of this disease: interferon-beta-1a (IFN β-1a) (AVONEX®, Biogen, Inc., Cambridge, Mass. and REBIF®, Serono, Geneva, Switzerland) and interferon-beta-1b (IFN β-1a) (BETASERON®, Berlex, Richmond, Calif.). AVONEX® and REBIF® are produced in mammalian cells using the natural human gene sequence and is glycosylated, whereas BETASERON® is produced in *E. coli* bacteria using a modified human gene sequence that contains a genetically engineered cysteine-to-serine substitution at amino acid position 17 and is non-glycosylated.

Non-immune interferons, which include both alpha and beta interferons, are known to suppress human immunodeficiency virus (HIV) in both acutely and chronically-infected cells. See Poli and Fauci, 1992, *AIDS Research and Human Retroviruses* 8(2):191-197. Due to their antiviral activity, interferons, in particular alpha interferons, have received considerable attention as therapeutic agents in the treatment of hepatitis C virus (HCV)-related disease. See Hoofnagle et al., in: Viral Hepatitis 1981 International Symposium, 1982, Philadelphia, Franklin Institute Press; Hoofnagle et al., 1986, *New Eng J Med* 315:1575-1578; Thomson, 1987, Lancet 1:539-541 Kiyosawa et al., 1983, in: Zuckerman, ed., *Viral Hepatitis and Liver Disease*, Allen K. Liss, New York pp. 895-897; Hoofnagle et al., 1985, *Sem Liv Dis*, 9:259-263.

Interferon-polymer conjugates, including conjugates with PEG, are described in, for example, U.S. Pat. Nos. 4,766, 106, 4,917,888, 8,017,733, European Patent No. 0 236 987, European Patent No. 0 510 356 and International Application Publication No. WO 95/13090.

Chronic hepatitis C is an insidious and slowly progressive disease having a significant impact on the quality of life. Despite improvement in the quality of the blood-donor pool and the recent implementation of testing of donated blood for HCV, the estimated incidence of acute infection among persons receiving transfusions is 5 to 10%. See Alter et al., in: Zuckerman, ed., Viral Hepatitis and Liver Disease, Allen K. Liss, New York. 1988, pp. 537-542. Thus, of the approximately 3 million persons who receive transfusions in the United States each year, acute hepatitis C will develop in about 150,000. While many patients who contract hepatitis C will have subclinical or mild disease, approximately 50% will progress to a chronic disease state characterized by fluctuating serum transaminase abnormalities and inflammatory lesions on liver biopsy. It is estimated that cirrhosis will develop in up to about 20% of this group. See Koretz et al., 1985, Gastroenterology 88:1251-1254.

Interferons are known to affect a variety of cellular functions, including DNA replication, and RNA and protein synthesis, in both normal and abnormal cells. Thus, cytotoxic effects of interferon are not restricted to tumor or virus-infected cells but are also manifested in normal, healthy cells. As a result, undesirable side effects may arise during interferon therapy, particularly when high doses are required. Administration of interferon can lead to myelosuppression, thereby resulting in reduced red blood cell count, and reduced white blood cell and platelet levels. Interferons commonly give rise to flu-like symptoms (e.g., fever, fatigue, headaches and chills), gastrointestinal disorders (e.g., anorexia, nausea and diarrhea), dizziness and coughing. Often, the sustained response of HCV patients to non-PEGylated interferon treatment is low and the treatment can induce severe side effects, including, but not limited to, retinopathy, thyroiditis, acute pancreatitis, and depression.

U.S. Pat. No. 8,017,733 describes the synthesis of activated polyalkylene glycols, including 20 kDa mPEG-O-2methylpropionaldehyde, and their use in making conjugates with interferon, including PEGylated IFN β-1a. In one example, human IFN β-1a was PEGylated at its N-terminus with 20 kDa mPEG-O-2-methylpropionaldehyde. The starting material in this process was non-formulated AVONEX®, i.e., IFN β-1a bulk intermediate which was a clinical batch of bulk drug which had passed all tests for use in humans. The product of the reductive alkylation chemistry used to incorporate the PEG onto the IFN β-1a backbone resulted in the formation of an amine linkage which is extremely stable against degradation. This product has been shown to have improved pharmacokinetic parameters and in vivo efficacy in a melanoma angiogenesis model. See Baker et al., 2006, *Bioconjug Chem* 17(1):179-188.

Relapsing-remitting multiple sclerosis (RRMS) is characterized by clearly defined attacks of worsening neurologic function. These attacks—often called relapses, flare-ups or exacerbations—are followed by partial or complete recovery periods (remissions), during which symptoms improve partially or completely, and there is no apparent progression of disease. RRMS is the most common disease course at the time of diagnosis. Approximately 85 percent of people are initially diagnosed with RRMS, compared to 10-15 percent with progressive forms of the disease. PEGylated interferon β-1a (PLEGRIDY™) has been approved in the United States and in Europe for treating relapsing-remitting multiple sclerosis.

It is desired to develop and utilize a PEGylation reaction (also referred to herein as a PEG coupling reaction) that can be integrated into a biopharmaceutical process or in a batch process for ease of manufacturing, improved throughput and improved handling of reaction reagents and products.

SUMMARY OF THE INVENTION

The present invention relates to a method for PEGylating interferon beta (IFN β). In one embodiment, the IFN β is IFN β-1a. In another embodiment, the IFN β is IFN β-1b.

Thus, one aspect of the present invention provides a process for coupling PEG to IFN. In one embodiment, a process for coupling PEG to IFN β comprises the following steps:

(a) adding activated PEG to a purified IFN β solution in a reaction vessel to form a mixture of activated PEG and IFN β, wherein the purified IFN β solution has a concentration of IFN β from about 0.5 mg/ml to about 4.7 mg/ml and a temperature of from about 2° C. to about 30° C., wherein the amount of activated PEG added is sufficient to provide a molar ratio of activated PEG to IFN β in a PEG coupling reaction mixture from about 1:1 to about 20:1 and wherein the pH of the mixture is from about 4.0 to about 6.0;

(b) optionally adding a Lewis acid catalyst to the mixture, wherein the amount of Lewis acid catalyst when added is sufficient to provide a concentration of Lewis acid catalyst in the PEG coupling reaction mixture from about 0.1 mM to about 2.2 mM;

(c) adding $NaCNBH_3$ to the mixture to form the PEG coupling reaction mixture with stirring over a period of about 5 minutes to about 600 minutes, wherein the amount of $NaCNBH_3$ added is sufficient to provide a concentration of $NaCNBH_3$ in the PEG coupling reaction mixture from about 5 mM to about 100 mM; and (d) incubating the PEG coupling reaction mixture for about 10 minutes to about 24 hours to produce preferentially mono-PEG IFN β.

In one embodiment, a Lewis acid catalyst is added to the reaction mixture. In another embodiment, the Lewis acid catalyst is a zinc cation. In a further embodiment, the process further comprises quenching the PEG coupling reaction to stop the reaction. In one embodiment, the PEG coupling reaction is quenched by adding arginine. In another embodiment, the amount of arginine in the quenched reaction mixture is from about 25 mM to about 250 mM.

In one embodiment, the purified IFN β solution is brought to the desired temperature before it is added to a reaction vessel. In another embodiment, the purified IFN β solution is added to the reaction vessel and brought to the desired temperature before the activated PEG is added. In a further embodiment, the various mixtures in the reaction vessel are overlaid with an inert gas. In one embodiment, the inert gas is argon. In another embodiment, the inert gas is nitrogen. In one embodiment, the IFN β is IFN β-1a. In another embodiment, the IFN β is IFN β-1b. In one embodiment, the PEG is mPEG. In one embodiment, the activated PEG is PEG-O-2-methylpropionaldehyde. In another embodiment, the activated PEG is mPEG-O-2-methylpropionaldehyde. In one embodiment, the PEG has a molecular weight of about 20 kDa.

The PEG IFN β is purified using conventional techniques. Thus, in one embodiment, the present invention also provides a PEG IFN β purified from the PEG coupling reaction or the quenched PEG coupling reaction obtained in accordance with the process of this embodiment.

In another embodiment, a process for coupling PEG to IFN β comprises the following steps:

(a) adding an activated PEG to a purified IFN β solution in a reaction vessel to form a mixture of activated PEG and IFN β, wherein the purified IFN β solution has a concentration of IFN β from about 1.75 mg/ml to about 3.3 mg/ml and a temperature of from about 19° C. to about 27° C., wherein the amount of activated PEG added is sufficient to provide a molar ratio of PEG to IFN β from about 1:1 to about 5:1 and wherein the pH is from about 4.8 to about 5.2;

(b) optionally adding a Lewis acid catalyst to the mixture, wherein the amount of Lewis acid catalyst when added is sufficient to provide a concentration of Lewis acid catalyst in the PEG coupling reaction mixture from about 0.78 mM to about 1.2 mM;

(c) adding $NaCNBH_3$ to the mixture to form the PEG coupling reaction mixture with stirring over a period of about 45 minutes to about 240 minutes, wherein the amount of $NaCNBH_3$ added is sufficient to provide a concentration of $NaCNBH_3$ in the PEG coupling reaction mixture from about 15 mM to about 25 mM; and (d) incubating the PEG coupling reaction mixture for about 5 hours to about 9 hours to preferentially produce mono-PEG IFN β.

In one embodiment, the process further comprises quenching the PEG coupling reaction to stop the reaction. In another embodiment, the PEG coupling reaction is quenched by adding arginine. In one embodiment the amount of arginine that is added is sufficient to provide a concentration of arginine in the quenched PEG coupling reaction mixture from about 50 mM to about 150 mM. In another embodiment, the amount of arginine that is added is sufficient to provide a concentration of arginine in the quenched PEG coupling reaction mixture from about 75 mM to about 125 mM. In a further embodiment, the amount of arginine that is added is sufficient to provide a concentration of arginine in the quenched PEG coupling reaction mixture of about 100 mM. In a further embodiment, the various mixtures in the reaction vessel are overlaid with an inert gas. In one embodiment, the inert gas is argon. In another embodiment, the inert gas is nitrogen.

In one embodiment, the purified IFN β solution is brought to the desired temperature before it is added to a reaction vessel. In another embodiment, the purified IFN β solution is added to the reaction vessel and brought to the desired temperature before the activated PEG is added.

In one embodiment, the concentration of IFN β in the purified IFN β solution is from about 1.75 mg/ml to about 3.3 mg/ml. In another embodiment, the concentration of IFN β in the purified IFN β solution is from about 2.0 mg/ml to about 3.3 mg/ml. In a further embodiment, the concentration of IFN β in the purified IFN β solution is from about 2.4 mg/ml to about 3.3 mg/ml. In an additional embodiment, the concentration of IFN β in the purified IFN β solution is from about 2.9 mg/ml to about 3.3 mg/ml. In another embodiment, the concentration of IFN β in the purified IFN β solution is about 3.3 mg/ml. In one embodiment, the IFN β is IFN β-1a. In another embodiment, the IFN β is IFN β-1b.

In one embodiment, the molar ratio of activated PEG to IFN β in the PEG coupling reaction mixture is from about 1.5:1 to about 5:1. In another embodiment, the molar ratio of activated PEG to IFN β in the PEG coupling reaction mixture is from about 1.5:1 to about 2:1. In a further embodiment, the molar ratio of activated PEG to IFN β in the PEG coupling reaction mixture is about 1.5:1. In one embodiment, the PEG is mPEG. In one embodiment, the activated PEG is PEG-O-2-methylpropionaldehyde. In another embodiment, the activated PEG is mPEG-O-2-methylpropionaldehyde. In one embodiment, the PEG has a molecular weight of about 20 kDa.

In one embodiment, the Lewis acid catalyst is added to the reaction mixture. In another embodiment, the Lewis acid catalyst is a zinc cation. In one embodiment, the concentration of the Lewis acid catalyst or the zinc cation in a PEG coupling reaction mixture is from about 0.78 mM to about 1.2 mM. In another embodiment, the concentration of the Lewis acid catalyst or the zinc cation in a PEG coupling reaction mixture is from about 0.9 mM to about 1.1 mM. In a further embodiment, the concentration of the Lewis acid catalyst or the zinc cation in a PEG coupling reaction mixture is from about 0.95 mM to about 1.05 mM. In an additional embodiment, the concentration of the Lewis acid catalyst or the zinc cation in a PEG coupling reaction mixture is about 1.0 mM.

In one embodiment, the concentration of $NaCNBH_3$ in a PEG coupling reaction mixture is from about 15 mM to about 25 mM. In another embodiment, the concentration of $NaCNBH_3$ in a PEG coupling reaction mixture is from about 18 mM to about 22 mM. In a further embodiment, the concentration of $NaCNBH_3$ in a PEG coupling reaction mixture is about 20 mM.

Although not a critical or key parameter (as described herein) for the PEG coupling reagent, the hold time of the quenched PEG coupling reaction mixture is critical for maximizing the amount of purified mono-PEG IFN β recovered from the PEG coupling reaction mixture. The quenched PEG coupling reaction mixture can be held for up to 48 hours at about 2° C. to about 25° C. before initiating purification of the mono-PEG IFN β. In one embodiment, the hold temperature is about 18° C. to about 25° C., preferably about 20° C. to about 23° C. In another embodiment, the hold temperature is about 2° C. to about 8° C. In a further embodiment, the hold temperature is about 8° C. to about 18° C. The PEG IFN β is purified using conventional techniques. Thus, in one embodiment, the present invention also provides a PEG IFN β purified from the PEG coupling reaction or the quenched PEG coupling reaction obtained in accordance with the process of this embodiment.

In a second aspect, the present invention provides a PEG coupling reaction mixture. In one embodiment, a PEG coupling reaction mixture comprises the following elements:

(a) IFN β at a concentration from about 0.4 mg/ml to about 4.0 mg/ml;

(b) activated PEG at a molar ratio of activated PEG to IFN β from about 1:1 to about 20:1; and (c) $NaCNBH_3$ at a concentration from about 5 mM to about 100 mM, wherein the pH of the PEG reaction mixture is from about 4.0 to about 6.0.

In one embodiment, the PEG coupling reaction mixture further comprises a Lewis acid catalyst at a concentration from about 0.1 mM to about 2.2 mM. In another embodiment, the Lewis acid catalyst is a zinc cation. In a further embodiment, the PEG coupling reaction mixture further comprises arginine at a concentration in the reaction mixture from about 25 mM to about 250 mM. In one embodiment, the PEG coupling reaction mixture further comprising arginine is quenched. In a further embodiment, the PEG coupling reaction mixture in the reaction vessel is overlaid with an inert gas. In one embodiment, the inert gas is argon. In another embodiment, the inert gas is nitrogen. In one embodiment, the IFN β is IFN β-1a. In another embodiment, the IFN β is IFN β-1b. In one embodiment, the PEG is mPEG. In one embodiment, the activated PEG is PEG-O-2-methylpropionaldehyde. In another embodiment, the activated PEG is mPEG-O-2-methylpropionaldehyde. In one embodiment, the PEG has a molecular weight of about 20 kDa.

The PEG IFN β is purified using conventional techniques. Thus, in one embodiment, the present invention also provides a PEG IFN β purified from the PEG coupling reaction or the quenched PEG coupling reaction obtained in accordance with this embodiment.

In another embodiment, a PEG coupling reaction mixture comprises the following elements:

(a) IFN β at a concentration from about 1.5 mg/ml to about 2.8 mg/ml, preferably from about 2.0 mg/ml to about 2.8 mg/ml, more preferably from about 2.5 mg/ml to about 2.8 mg/ml, more preferably about 2.8 mg/ml;

(b) activated PEG at a molar ratio of activated PEG to IFN β from about 1:1 to about 5:1, preferably from about 1.5:1 to about 5:1, more preferably from about 1.5:1 to about 2:1, still more preferably about 1.5:1; and (c) NaCNBH$_3$ at a concentration from about 15 mM to about 25 mM, preferably from about 18 mM to about 22 mM, more preferably about 20 mM, wherein the pH of the PEG coupling reaction mixture is from about 4.8 to about 5.2, preferably from about 4.9 to about 5.1, more preferably about 5.0.

In one embodiment, the PEG coupling reaction further comprises a Lewis acid catalyst at a concentration from about 0.78 mM to about 1.2 mM, preferably from about 0.9 mM to about 1.1 mM, more preferably from about 0.95 mM to about 1.05 mM, still more preferably about 1.0 mM. In another embodiment, the Lewis acid catalyst is a zinc cation.

In a further embodiment, the PEG coupling reaction mixture further comprises arginine at a concentration in the reaction mixture from about 50 mM to about 150 mM, preferably from about 75 mM to about 125 mM, more preferably about 100 mM. In one embodiment, the PEG coupling reaction mixture further comprising arginine is quenched. In another embodiment, the PEG coupling reaction mixture is in a reaction vessel. In a further embodiment, the PEG coupling reaction mixture in the reaction vessel is overlaid with an inert gas. In one embodiment, the inert gas is argon. In another embodiment, the inert gas is nitrogen. In one embodiment, the IFN β is IFN β-1a. In another embodiment, the IFN β is IFN β-1b. In one embodiment, the PEG is mPEG. In one embodiment, the activated PEG is PEG-O-2-methylpropionaldehyde. In another embodiment, the activated PEG is mPEG-O-2-methylpropionaldehyde. In one embodiment, the PEG has a molecular weight of about 20 kDa.

In one embodiment, the IFN β is IFN β-1a. In another embodiment, the IFN β is IFN β-1b. In one embodiment, the PEG is mPEG. In one embodiment, the activated PEG is PEG-O-2-methylpropionaldehyde. In another embodiment, the activated PEG is mPEG-O-2-methylpropionaldehyde. In one embodiment, the PEG has a molecular weight of about 20 kDa.

The PEG IFN β is purified using conventional techniques. Thus, in one embodiment, the present invention also provides a PEG IFN β purified from the PEG coupling reaction or the quenched PEG coupling reaction obtained in accordance with this embodiment.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE FIGURE

The FIGURE illustrates one embodiment of a PEG coupling reaction described herein.

DETAILED DESCRIPTION OF THE INVENTION

The present invention relates to a method for PEGylating interferon beta. In one embodiment, the IFN β is IFN β-1a. In another embodiment, the IFN β is IFN β-1b.

The term "interferon" or "IFN" as used herein means the family of highly homologous species-specific proteins that inhibit viral replication and cellular proliferation and modulate immune response. Human interferons are grouped into two classes; Type I, including α- and β-interferon, and Type II, which is represented by γ-interferon only. Recombinant forms of each group have been developed and are commercially available. Subtypes in each group are based on antigenic/structural characteristics.

The terms "beta interferon", "beta-interferon", "beta IFN", "beta-IFN", β interferon", "β-interferon", "β IFN", "IFN", "interferon beta", "interferon-beta", "interferon β", "interferon-β", "IFN beta", "IFN-beta", "IFN β", "IFN β", and "human fibroblast interferon" are used interchangeably herein to describe members of the group of interferon beta's which have distinct amino acid sequences as have been identified by isolating and sequencing DNA encoding the peptides.

Additionally, the terms "beta interferon 1a", "beta interferon-1a" "beta-interferon 1a", "beta-interferon-1a", "beta IFN 1a", "beta IFN-1a", "beta-IFN 1a", "beta-IFN-1a", "β interferon 1a", "β interferon-1a", "β-interferon 1a", "β-interferon-1a", "β IFN 1a", "β IFN-1a", "β-IFN 1a", "β-IFN-1a", "interferon beta 1a", "interferon beta-1a", "interferon-beta 1a", "interferon-beta-1a", "interferon β 1a", "interferon β-1a", "interferon-β 1a", "interferon-β-1a", "IFN beta 1a", "IFN beta-1a", "IFN-beta 1a", "IFN-beta-1a", "IFN β 1a", "IFN β-1a", "IFN β 1a" and, "IFN β-1a" are used interchangeably herein to describe recombinantly- or synthetically-produced interferon beta that has the naturally-occurring (wild type) amino acid sequences.

Additionally, the terms "beta interferon 1b", "beta interferon-1b" "beta-interferon 1b", "beta-interferon-1b", "beta IFN 1b", "beta IFN-1b", "beta-IFN 1b", "beta-IFN-1b", "β interferon 1b", "β interferon-1b", "β-interferon 1b", "β-interferon-1b", "β IFN 1b", "β IFN-1b", "β-IFN 1b", "β-IFN-1b", "interferon beta 1b", "interferon beta-1b", "interferon-beta 1b", "interferon-beta-1b", "interferon β 1b", "interferon β-1b", "interferon-β 1b", "interferon-β-1b", "IFN beta 1b", "IFN beta-1b", "IFN-beta 1b", "IFN-beta-1b", "IFN β 1b", "IFN β-1b", "IFN β 1b" and, "IFN β-1a" are used interchangeably herein to describe recombinantly- or synthetically-produced interferon beta that has the naturally-occurring (wild type) amino acid sequences.

The terms "PEGylated IFN beta", "PEGylated IFN-beta", "PEGylated IFN β", "PEGylated IFN β", "PEGylated interferon beta", "PEGylated interferon-beta", "PEGylated interferon β", "PEGylated interferon-β", "PEG IFN beta", "PEG IFN-beta", "PEG IFN β", "PEG IFN β", "PEG interferon beta", "PEG interferon-beta", "PEG interferon β" and "PEG interferon-β" are used interchangeably herein to describe an IFN beta which contains a PEG or mPEG moiety linked to the amino terminus of the interferon.

The term "preferentially mono-PEG IFN β" is used herein to mean that more than 50% of this product is present in the quenched reaction mixture. In some embodiments, the yield of mono-PEG IFN β is from about 62% to about 68% of the PEGylated product.

The term "activated-PEG" refers to a PEG which has been activated by preparing a derivative of PEG having a reactive functional group on at least one terminus. The reactive functional group is chosen based on the type of available reactive group on the molecule that will be coupled to the PEG. Examples of activated PEG are well known in the art, such as described in U.S. Pat. No. 8,017,733.

The advent of recombinant DNA technology applied to interferon production has permitted several human interferons to be successfully synthesized, thereby enabling the large-scale fermentation, production, isolation, and purification of various interferons to homogeneity. Recombinantly produced interferon retains some—or most of—its in vitro and in vivo antiviral and immunomodulatory activities. It is also understood that recombinant techniques could also include a glycosylation site for addition of a carbohydrate moiety on the recombinantly-derived polypeptide.

The construction of recombinant DNA plasmids containing sequences encoding at least part of human fibroblast interferon and the expression of a polypeptide having immunological or biological activity of human fibroblast interferon is also contemplated. The construction of hybrid beta-interferon genes containing combinations of different subtype sequences can be accomplished by techniques known to those of skill in the art.

As described in U.S. Pat. No. 8,017,733, IFN β can be PEGylated by reacting a solution of IFN β-1a, which had been obtained by applying a batch of IFN β to a SF-Sepharose FF column and recovering the IFN β from the column, with an mPEG-O-2-methylpropionaldehyde at pH 6.0 in the presence of sodium cyanoborohydride at room temperature for 16 hr in the dark. The PEGylated IFN β was then purified using a SF-Sepharose FF column followed by a Superose 6HR 10/20 FPLC sizing column.

In order to develop a PEGylation reaction that could be integrated into a biopharmaceutical process or in a batch process for ease of manufacturing, improved throughput and improved handling of reaction reagents and products, the parameters of PEGylation reactions were examined to identify those parameters which are important to the quality of the PEGylated IFN β product, namely an IFN β linked to a single PEG molecule at the N-terminus. In one embodiment the PEG molecule is preferably a PEG molecule having a molecular weight of 20 kDa. In another embodiment, the PEG is mPEG. The parameters which are important for product quality are sometimes referred to herein as critical parameters. The parameters which are important for yield or consistency of the product are sometimes referred to herein as key parameters. A parameter can be both a critical parameter and a key parameter.

It is well known that IFN β, including IFN β-1a and IFN β-1b, is a somewhat labile protein with well understood mechanisms of degradation. The primary mechanisms of degradation after cell culture harvest are soluble aggregate formation and deamidation, especially at elevated temperatures (i.e., >20° C.) and pH≥7.5. Consequently, the purification process of recombinantly produced IFN β is typically carried out to minimize IFN β degradation by using a low temperature, such as about 2° C. to about 8° C.

It is also known that PEG IFN β has similar mechanisms of degradation as IFN β with two additional mechanisms of degradation. The potential for the O-2-methylpropionyl linker (the 3 carbon moiety that, in some embodiments, attaches the 20 kDa mPEG to the N-terminus of IFN β) to cleave has been shown to occur at elevated temperature (i.e., 40° C.), which results in the generation of free IFN β. In addition, the 20 kDa mPEG moiety can undergo oxidative degradation in the presence of peroxides, leading to a shortened chain resulting in increased polydispersity (i.e., lower molecular weight). Consequently, the purification process of PEG IFN β is typically carried out to minimize PEG IFN β degradation by using a ambient temperature, e.g. room temperature.

A thorough analysis and study of the parameters of PEGylation reactions was performed in which 20 kDA mPEG-O-2-methylpropionaldehyde was used as the activated PEG molecule and IFN β-1a was used as the IFN β, solely for the purpose of this analysis. However, it is understood that IFN β-1b and other activated PEG molecules could have been used for this analysis and study. For example, the reaction temperature was studied and it was found that the coupling reaction was temperature dependent. The developmental data demonstrated that a temperature between about 2° C. and about 30° C. could be used. At 2° C., the reaction proceeds slowly. At 30° C., the product aggregates quicker. In a preferred embodiment, it was found that if the temperature decreases below an action limit of 19° C., the kinetics of the reaction will decrease and mono-PEG IFN β conversion will be lower than expected. In this preferred embodiment, it was found that if the temperature exceeds an action limit of 27° C., incorrect product profiles will be expected (higher than normal multi-PEG IFN β, lower than normal unreacted IFN β) and the product can potentially aggregate. In view of this study and particularly with respect to a preferred embodiment of the present invention, it was determined that the coupling reaction temperature is a critical/key parameter.

The amount of activated PEG in the PEG coupling reaction was also studied. In this study, the initial target addition volume for a PEG stock solution was set to 1 L (or 1007 grams+/−50 grams) based on the solution volume of IFN β used for the study. The stock solution was prepared to achieve a molar ratio of PEG to IFN β of 1:1 to 20:1 in the final reaction mixture (i.e., the PEG coupling reaction mixture after the addition of the NaCNBH$_3$), based on the reported activity of the mPEG lot from the vendor. The study showed that there is flexibility in the total amount of activated mPEG that is required to achieve a maximal mono-PEG conversion, allowing for a broader amount of activated mPEG for a molar ratio of mPEG:IFN β between 1:1 and 20:1. In a preferred embodiment, it was found that a range of concentration of activated mPEG of 4.0-5.5 mg/ml in the final reaction mixture could be used without affecting the overall mono-PEG IFN β yield. In this preferred embodiment, it was found that if the amount of activated mPEG is below 4.0 mg/ml or above 5.5 mg/ml, the yield of mono-PEG was reduced. In view of this study and particularly with respect to a preferred embodiment of the present invention, it was determined that the amount of activated mPEG in the PEG coupling reaction is a key parameter.

It has been shown that the addition of $ZnCl_2$ to the PEG coupling reaction mixture was beneficial for improving mono-PEG conversion due to its known role as a Lewis acid catalyst in several redox reactions (Kim, S et al., 1985, *J Org Chem* 50(11):1927-1931). Although not necessary for the PEGylation reaction to proceed (e.g., the reaction proceeds but with slightly lower yield) and thus an optional reagent in the PEG coupling reaction, the use of a Lewis acid catalyst, such as $ZnCl_2$, in the PEG coupling reaction was studied. Experiments confirmed that 1 mM $ZnCl_2$ in the coupling mixture led to improved mono-PEG IFN levels by 10% and a stable reaction (slow rate of multi-PEG increase). In a preferred embodiment of the present invention, it was found that the addition of a Lewis acid catalyst eliminated the need for the slow addition of $NaCNBH_3$ (previously used to improve mono-PEG conversion and reduced the required amount of $NaCNBH_3$) because the activated aldehyde (potentially aided by a zinc-modified $NaCNBH_3$) was more efficiently converted to mono-PEG IFN. In some embodiments, other well-known Lewis acid catalysts can be used in place of $ZnCl_2$ in those embodiments for which a Lewis acid catalyst is desired.

In a preferred embodiment, the amount of $ZnCl_2$ in the PEG coupling reaction mixture was further studied. The study showed that there is flexibility in the total amount of a Lewis acid catalyst, such as zinc cations, that can be used in the reaction. If the optional Lewis acid catalyst is used, it is used in an amount from about 0.1 mM to 2.2 mM. In a preferred embodiment, it was found that a 1 mM concentration of a Lewis acid catalyst, such as zinc chloride, was optimal for achieving maximal mono-PEG IFN conversion. In this study, the target addition volume (1 L or 988 grams+/−50 grams), based on the solution volume of IFN β used for the study, of the 20 mM $ZnCl_2$ stock was designed to bring the final reaction mixture (i.e., the PEG coupling reaction mixture after the addition of the $NaCNBH_3$) to 1 mM $ZnCl_2$ in the final reaction mixture. While 1 mM $ZnCl_2$ was optimal in this preferred embodiment, concentrations between 0.78 mM and 1.2 mM in the final reaction mixture were found to yield acceptable mono-PEG IFN levels. In this preferred embodiment, it was found that if the amount of $ZnCl_2$ is below 0.78 mg/ml or above 1.2 mg/ml, the yield of mono-PEG was reduced. In view of this study and particularly with respect to this preferred embodiment of the present invention, it was determined that the amount of a Lewis acid catalyst, such as zinc cation, e.g., $ZnCl_2$, in the PEG coupling reaction is a key parameter.

Initially, operating pH was set between 4.0 and 6.0. Although the PEGylation reaction occurs throughout this range, it was found that at pH of 4.0, cyanide gas is emitted and the reaction is unstable. It was also found that at pH 6.0, the reaction is slower and more side reactions occur. It was further found that at an operating pH of 5.5 minimized $HCN/H_2$ off-gassing, but it resulted in some precipitation of $ZnCl_2$ and IFN β. Thus, in a preferred embodiment the pH useful for the addition of $ZnCl_2$ was studied. In this preferred embodiment, it was found that a pH of 4.6 to 5.2 was suitable to prevent precipitation of the $ZnCl_2$ and the IFN β. If the pH was above 5.2, it was found that the yield of mono-PEG was reduced. In addition, in a preferred embodiment it was found that a pH of 4.8 to 5.2 was suitable for the addition of $NaCNBH_3$. If the pH was below 4.8 or above 5.2, it was found that the yield of mono-PEG was reduced. It was also found that a preferred pH was 5.0 for the addition of each reagent and coupling reaction. Therefore, the buffers used throughout the process were changed in a preferred embodiment to accommodate a coupling reaction pH of 5.0. In view of this study and particularly with respect to a preferred embodiment of the present invention, it was determined that the pH of the reaction mixture for the addition of $ZnCl_2$ in the PEG coupling reaction is a key parameter. It was also determined that the pH of the reaction mixture for the addition of $NaCNBH_3$ in the PEG coupling reaction is a key parameter with respect to a preferred embodiment of the present invention.

The amount of $NaCNBH_3$ in the PEG coupling reaction was also studied. In this study, the target addition volume for the 400 mM $NaCNBH_3$ stock solution was designed to be 1 L (1025 grams+/−50 grams) for all batches, based on the solution volume of IFN β used for the study. The 1 L volume of $NaCNBH_3$ stock solution was based on a final $NaCNBH_3$ concentration of 5 mM to 100 mM, the range for which it was found that the reaction occurred. It was found that the reaction did not go to completion and the reaction product was unstable below 5 mM $NaCNBH_3$. It was also found that the reaction went too fast with low yield above 100 mM. In a preferred embodiment, a final concentration of 20 mM in the reaction mixture (i.e., the PEG coupling reaction mixture after the addition of the $NaCNBH_3$) was chosen for study. This study indicated that a range of 15 mM-25 mM $NaCNBH_3$ was preferred. If the amount of $NaCNBH_3$ was below 15 mM, it was found that the yield of mono-PEG was reduced. Care should be taken to avoid over-addition of the $NaCNBH_3$ stock, to reduce the level of HCN and $H_2$ off-gassing. In view of this study and particularly with respect to a preferred embodiment of the present invention, it was determined that the amount of $NaCNBH_3$ in the PEG coupling reaction is a key parameter.

The time for the addition of $NaCNBH_3$ to the PEG coupling reaction was also studied. In this study, the time for adding $NaCNBH_3$ to the reaction mixture was analyzed for times greater than 1 min. It was found that the rate of $NaCNBH_3$ addition was insignificant in the presence of zinc chloride. Thus, longer $NaCNBH_3$ addition periods did not significantly affect product conversion. A lower limit of 5 min was chosen. An upper limit of 600 min was arbitrarily chosen to provide an otherwise limit on the time of addition. In a preferred embodiment, it was found that the yield of mono-PEG was reduced for a time of less than 45 min for the addition $NaCNBH_3$. An upper limit of 240 min was selected to provide a reasonable time for the addition of $NaCNBH_3$. In view of this study and particularly with respect to a preferred embodiment of the present invention, it was determined that the time for the addition of $NaCNBH_3$ in the PEG coupling reaction is a key parameter.

The amount of IFN β in the reaction mixture was also studied. The amount of IFN β in the PEG coupling reaction after the addition of the $NaCNBH_3$ was studied for the effect on the amount of mono-PEG produced. It was found that the process worked for a range of 0.4 mg/ml to about 4.0 mg/ml of IFN β, which corresponds to a range of 0.5 mg/ml to about 4.7 mg/ml in the purified IFN β solution. At 4.0 mg/ml and above, the reaction failed because of precipitation. In a preferred embodiment, it was found that an IFN β concentration of more than 2.8 mg/ml in the final PEG coupling reaction (i.e., the PEG coupling reaction mixture after the addition of the $NaCNBH_3$) resulted in a lower yield caused by precipitation. The 2.8 mg/ml concentration of IFN β in the final PEG coupling reaction corresponds to a 3.3 mg/ml concentration of IFN β in the initial purified protein solution used for the PEGylation coupling reaction. It was found that concentrations of IFN β lower than 1.5 mg/ml in the final PEG coupling reaction (corresponding to 1.75 mg/ml of IFN β in the initial purified protein solution) led to increased multi-PEG IFN β, some of which could be tolerated if removed in downstream purification. For example, an IFN β concentration of 1.36 mg/ml in the final PEG coupling reaction (corresponding to 1.6 mg/ml IFN β in initial purified protein solution) resulted in 20% multi-PEG IFN β compared to 18% at a concentration of 1.5 mg/ml. In view of this study and particularly, it was determined that the amount of IFN β in the reaction mixture is a key parameter.

The hold time post addition of NaCNBH₃ (sometimes referred to herein as incubation or reaction time) was also studied. In this study, the reaction was quenched at various times after the addition of NaCNBH₃. Quenching was accomplished using arginine. Quenching the at 10 min provided less than 20% yield. Development data indicated that the coupling reaction begins to plateau early on (~200 minutes) implying that quenching after 200 minutes should lead to lower mono-PEG IFN β conversion. However, yield of mono-PEG IFN β could be obtained up to a reaction time of 24 hr. Although quenching the reaction early may lead to incomplete mono-PEG IFN β conversion (increased unreacted IFN β and thus decreased product yield and decreased multi-PEG IFN β), it should not have an impact of product quality. In a preferred embodiment, quenching the reaction after the 9-hour period leads to increased levels of multi-PEG IFN β. It is preferred to turn off the agitation during the reaction hold, to avoid excessive shear on the protein during the reaction. Based on an analysis of the data points for this preferred embodiment, it was concluded that a reaction time less than 5 hr resulted lower yield of mono-PEG IFN β and consequent higher levels of IFN β, whereas a reaction time greater than 9 hr resulted in higher levels of high molecular weight forms. In view of this study and particularly with respect to a preferred embodiment of the present invention, it was determined that the hold time post addition of NaCNBH₃ is a critical/key parameter.

The quenched reaction expiration time was also studied to determine the stability of the quenched reaction mixture until the mono-PEG IFN β was purified. It was found that the quenched reaction was stable in the reaction vessel for up to 48 hr at about 2° C. to about 30° C. In a preferred embodiment, the hold temperature is from about 2° C. to about 30° C. It was found that high molecular weight forms were produced if the time was greater than 48 hr. In view of this study, it was determined that the quenched reaction expiration time is a critical parameter with respect to the purification of the mono-PEG IFN β.

In view of these studies, the parameters for a preferred embodiment of the present invention that were found to be critical and/or key as defined herein for the PEG coupling reaction and purification of the mono-PEG IFN β product are set forth in Table 1.

TABLE 1

Critical and/or Key Parameters in a Preferred Embodiment for IFN beta PEGylation

| Category | Parameter | Operating Range or Limits | Performance Parameter Affected | Quality Attribute Affected |
| --- | --- | --- | --- | --- |
| Critical/Key | Reaction Temp. | 19°-27° C. | Yield Reduced if <19° C. | High Molecular Weight Forms[a] if >27° C. |
| Key | Activated mPEG (Final Conc.) | 4.0-5.5 mg/ml[b] | Yield Reduced if <4.0 mg/mL or if >5.5 mg/mL | NA |
| Key (optional) | ZnCl₂ (Final Conc.) | 0.78-1.2 mM[b] | Yield Reduced if <0.78 mM or if >1.2 mM | NA |
| Key (optional) | pH For ZnCl₂ Addition | 4.6-5.2 | Yield Reduced if >5.2 | NA |
| Key | NaCNBH₃ (Final Conc.) | 15-25 mM[b] | Yield Reduced if <15 mM; High Level HCN and H₂ off-gassing if >25 mM | NA |
| Key | pH For NaCNBH₃ Addition | 4.8-5.2 | Yield Reduced if <4.8 or if >5.2 | NA |
| Key | NaCNBH₃ Addition Time | 45-240 min | Yield Reduced and Turbidity if <45 min | NA |
| Key | IFN Conc. During NaCNBH₃ Addition | 1.75-3.3 mg/ml[c] | Yield Reduced if >3.3 mg/ml | NA |
| Critical/Key | Hold Time Post NaCNBH₃ Addition | 5.0-9.0 hr | Yield Reduced if <5.0 hr | High Molecular Weight Forms if >9 hr; IFN if <5.0 hr |
| Critical (optional) | Quenched Reaction Expiration Time[d] | 0-48 hr | NA | High Molecular Weight Forms if >48 hr |

[a]High molecular weight forms include oligomers of PEGylated IFN and multi-PEGylated forms of IFN.
[b]Concentration expressed as the concentration of reactant in the final PEG reaction mixture after addition of all of the reactants.
[c]The concentration is expressed as the concentration of IFN β in the initial purified IFN β solution.
[d]This parameter is critical with respect to the purification of the mono-PEG IFN β product.

Thus, in one aspect, the present invention provides a PEG coupling reaction. In one embodiment, the PEG coupling reaction takes into consideration the experiments and data described above. In accordance with this embodiment of the present invention, a process for coupling PEG to IFN β comprises the following steps:

(a) adding activated PEG to a purified IFN β solution in a reaction vessel to form a mixture of activated PEG and IFN β, wherein the purified IFN β solution has a concentration of IFN β from about 0.5 mg/ml to about 4.7 mg/ml and a temperature of from about 2° C. to about 30° C., wherein the amount of activated PEG added is sufficient to provide a molar ratio of activated PEG to IFN β in a PEG coupling reaction mixture from about 1:1 to about 20:1 and wherein the pH of the mixture is from about 4.0 to about 6.0;

(b) optionally adding a Lewis acid catalyst to the mixture, wherein the amount of Lewis acid catalyst when added is sufficient to provide a concentration of Lewis acid catalyst in the PEG coupling reaction mixture from about 0.1 mM to about 2.2 mM;

(c) adding NaCNBH$_3$ to the mixture to form the PEG coupling reaction mixture with stirring over a period of about 5 minutes to about 600 minutes, wherein the amount of NaCNBH$_3$ added is sufficient to provide a concentration of NaCNBH$_3$ in the PEG coupling reaction mixture from about 5 mM to about 100 mM; and (d) incubating the PEG coupling reaction mixture for about 10 minutes to about 24 hours to produce preferentially mono-PEG IFN β.

In one embodiment, a Lewis acid catalyst is added to the reaction mixture. In another embodiment, the Lewis acid catalyst is a zinc cation. In a further embodiment, the process further comprises quenching the PEG coupling reaction to stop the reaction. In one embodiment, the PEG coupling reaction is quenched by adding arginine. In another embodiment, the amount of arginine in the quenched reaction mixture is from about 25 mM to about 250 mM.

In one embodiment, the various mixtures in the reaction vessel are overlaid with an inert gas. In a further embodiment, the inert gas is argon. In another embodiment, the inert gas is nitrogen. In one embodiment, the IFN β is IFN β-1a. In another embodiment, the IFN β is IFN β-1b. In one embodiment, the PEG is mPEG. In one embodiment, the activated PEG is PEG-O-2-methylpropionaldehyde. In another embodiment, the activated mPEG is mPEG-O-2-methylpropionaldehyde. In one embodiment, the PEG has a molecular weight of about 20 kDa.

The reagents are commercially purchased or are prepared using conventional techniques or are prepared as described herein. For example, 20 kDa mPEG-O-2-methylpropionaldehyde can be purchased from various suppliers, including for example, BioVectra and NOF Corporation, or it can be prepared as described in U.S. Pat. No. 8,017,733. The IFN β starting material is recombinantly produced, e.g., in a bioreactor, using conventional procedures and techniques and is purified for use in a PEG coupling reaction using conventional techniques.

In one embodiment, the recombinantly produced IFN β is purified using conventional techniques well known in the art using a temperature to reduce the degradation of IFN β, such as from about 2° C. to about 8° C. In addition, the buffers used during purification, such as in the final steps of purification are selected such that the purified IFN β solution will have the desired pH. The amount of purified IFN β in the solution is determined. If necessary the purified IFN β solution is diluted or concentrated to provide a solution having the desired IFN β concentration. The purified IFN β can be stored frozen at a −70° C. until used. If the purified IFN β solution is stored frozen, it can be brought to the desired temperature before adding to the reaction vessel. Alternatively, although less efficient, the frozen purified IFN β solution could be added to the reaction vessel and brought to the desired temperature.

In another embodiment, the recombinantly produced IFN β is purified using conventional techniques well known in the art using a temperature to reduce the degradation of IFN β, such as from about 2° C. to about 8° C. In this embodiment, an ultrafiltration/diafiltration (UF/DF) step is utilized to produce a purified IFN β solution having a constant volume of purified IFN β solution from each batch of recombinantly produced IFN β. The constant volume for the purified IFN β solution will also have the desired concentration of IFN β A constant volume of the purified IFN β solution enables the use of constant volumes of the reagents to ensure the proper reagent concentrations in the PEG coupling reaction which makes it easier to automate the production of mono-PEG IFN β and the integration of the PEG coupling reaction into a bioreactor process. These factors lead to better consistency in the PEGylation reaction and better consistency of the mono-PEG IFN β produced in the reaction. As described above, an appropriate buffer is utilized in this step so that the resulting purified IFN β solution has the desired pH for the PEG coupling reaction. In one embodiment, the purified IFN β solution following the UF/DF step is frozen and stored prior to use in a PEG coupling reaction. This frozen solution is brought to the desired temperature as described above. In another embodiment, the purified IFN β solution is added to a reaction vessel and brought to the desired temperature. In a further embodiment, the purified IFN β solution is brought to the desired temperature before adding to the reaction vessel.

The PEG IFN β is purified using conventional techniques or as described herein. Thus, in one embodiment, the present invention also provides a PEG IFN β purified from the PEG coupling reaction or the quenched PEG coupling reaction obtained in accordance with the process of this embodiment.

In a second embodiment, the PEG coupling reaction, illustrated in the FIGURE, takes into consideration the critical and/or key parameters set forth in Table 1. In accordance with this aspect of the present invention, a process for coupling PEG to IFN β comprises the following steps:

(a) adding an activated PEG to a purified IFN β solution in a reaction vessel to form a mixture of activated PEG and IFN β, wherein the purified IFN β solution has a concentration of IFN β from about 1.75 mg/ml to about 3.3 mg/ml and a temperature of from about 19° C. to about 27° C., wherein the amount of activated PEG added is sufficient to provide a molar ratio of PEG to IFN β from about 1:1 to about 5:1 and wherein the pH is from about 4.8 to about 5.2;

(b) optionally adding a Lewis acid catalyst to the mixture, wherein the amount of Lewis acid catalyst when added is sufficient to provide a concentration of Lewis acid catalyst in the PEG coupling reaction mixture from about 0.78 mM to about 1.2 mM;

(c) adding NaCNBH$_3$ to the mixture to form the PEG coupling reaction mixture with stirring over a period of about 45 minutes to about 240 minutes, wherein the amount of NaCNBH$_3$ added is sufficient to provide a concentration of NaCNBH$_3$ in the PEG coupling reaction mixture from about 15 mM to about 25 mM; and (d) incubating the PEG coupling reaction mixture for about 5 hours to about 9 hours to preferentially produce mono-PEG IFN β.

In one embodiment, the process further comprises quenching the PEG coupling reaction to stop the reaction. In another embodiment, the PEG coupling reaction is quenched by adding arginine. In one embodiment the amount of arginine that is added is sufficient to provide a concentration of arginine in the quenched PEG coupling reaction mixture from about 50 mM to about 150 mM. In another embodiment, the amount of arginine that is added is sufficient to provide a concentration of arginine in the quenched PEG coupling reaction mixture from about 75 mM to about 125 mM. In a further embodiment, the amount of arginine that is added is sufficient to provide a concentration of arginine in the quenched PEG coupling reaction mixture of about 100 mM. In a further embodiment, the various mixtures in the reaction vessel are overlaid with an inert gas. In one embodiment, the inert gas is argon. In another embodiment, the inert gas is nitrogen.

In one embodiment, the purified IFN β solution is brought to the desired temperature before added to a reaction vessel. In another embodiment, the purified IFN β solution is added to the reaction vessel and brought to the desired temperature before the activated PEG is added.

Although not a critical parameter for the PEG coupling reaction, the hold time of the quenched reaction is critical for maximizing the amount of purified mono-PEG IFN β recovered from the PEG coupling reaction.

The reagents are commercially purchased or are prepared using conventional techniques or are prepared as described herein. For example, 20 kDa mPEG-O-2-methylpropionaldehyde can be purchased from various suppliers, including for example, BioVectra and NOF Corporation, or it can be prepared as described in U.S. Pat. No. 8,017,733. The IFN β starting material is recombinantly produced, e.g., in a bioreactor, using conventional procedures and techniques and is purified for use in a PEG coupling reaction using conventional techniques.

In one embodiment, the recombinantly produced IFN β is purified using conventional techniques well known in the art using a temperature to reduce the degradation of IFN β, such as from about 2° C. to about 8° C. In addition, the buffers used during purification, such as in the final steps of purification are selected such that the purified IFN β solution will have a pH from about 4.8 to about 5.2, preferably from about 4.9 to about 5.1, more preferably about 5.0. The amount of purified IFN β in the solution is determined. If necessary the purified IFN β solution is diluted or concentrated to provide a solution having the desired IFN β concentration. In one embodiment, the concentration of IFN β in the purified IFN β solution is from about 1.75 mg/ml to about 3.3 mg/ml. In another embodiment, the concentration of IFN β in the purified IFN β solution is from about 2.0 mg/ml to about 3.3 mg/ml. In a further embodiment, the concentration of IFN β in the purified IFN β solution is from about 2.4 mg/ml to about 3.3 mg/ml. In an additional embodiment, the concentration of IFN β in the purified IFN β solution is from about 2.9 mg/ml to about 3.3 mg/ml. In another embodiment, the concentration of IFN in the purified IFN β solution is about 3.3 mg/ml. The purified IFN β can be stored frozen at a −70° C. until used. If the purified IFN β solution is stored frozen, it can be brought to the desired temperature before adding to the reaction vessel. Alternatively, although less efficient, the frozen purified IFN β solution could be added to the reaction vessel and brought to the desired temperature. In one embodiment, the IFN β is IFN β-1a. In another embodiment, the IFN β is IFN β-1b.

In another embodiment, the recombinantly produced IFN β is purified using conventional techniques well known in the art using a temperature to reduce the degradation of IFN β, such as from about 2° C. to about 8° C. In this embodiment, an ultrafiltration/diafiltration (UF/DF) step is utilized to produce a purified IFN β solution having a constant volume of purified IFN β solution from each batch of recombinantly produced IFN β. The constant volume for the purified IFN β solution will also have the desired concentration of IFN β, i.e., from about 1.75 mg/ml to about 3.3 mg/ml, preferably from about 2.4 mg/ml to about 3.3 mg·ml, more preferably from about 2.9 mg/ml to about 3.3 mg/ml, most preferably about 3.3 mg/ml. A constant volume of the purified IFN β solution enables the use of constant volumes of the reagents to ensure the proper reagent concentrations in the PEG coupling reaction which makes it easier to automate the production of mono-PEG IFN β and the integration of the PEG coupling reaction into a bioreactor process. These factors lead to better consistency in the PEGylation reaction and better consistency of the mono-PEG IFN β produced in the reaction. As described above, an appropriate buffer is utilized in this step so that the resulting purified IFN β solution has the desired pH for the PEG coupling reaction. In one embodiment, the purified IFN β solution following the UF/DF step is frozen and stored prior to use in a PEG coupling reaction. This frozen solution is brought to the desired temperature as described above. In another embodiment, the purified IFN β solution is added to a reaction vessel and brought to the desired temperature. In a further embodiment, the purified IFN β solution is brought to the desired temperature before adding to the reaction vessel. In one embodiment, the IFN β is IFN β-1a. In another embodiment, the IFN β is IFN β-1b.

In each of these embodiments, the purified IFN β solution, from the frozen stock or from the purified IFN β solution or in the reaction vessel, is brought to a temperature ranging from about 19° C. to about 27° C., preferably from about 21° C. to about 25° C., more preferably from about 22° C. to about 24° C., most preferably about 23° C. before addition of the activated PEG.

In a first step, activated PEG is added to the purified IFN β solution in the reaction vessel that is at the desired temperature and pH to form a mixture of activated PEG and IFN β. In one embodiment, the amount of activated PEG added to the purified IFN β solution is sufficient to provide molar ratio of activated PEG to IFN β in the PEG coupling reaction mixture is from about 1.5:1 to about 5:1. In another embodiment, the molar ratio of activated PEG to IFN β in the PEG coupling reaction mixture is from about 1.5:1 to about 2:1. In a further embodiment, the molar ratio of activated PEG to IFN β in the PEG coupling reaction mixture is about 1.5:1. When adding an activated PEG stock solution to the purified IFN β solution, care should be taken to ensure that the volume of the activated PEG stock solution that is added is only that necessary in order to ensure that the remaining reagents in the PEG coupling reaction will all reach the required levels. The rate of addition of the activated PEG stock solution was not found to be critical. The agitation rate is not a critical parameter in this step, but adequate mixing should preferably be achieved over a 14-16 minute period, to ensure adequate homogeneity of the reaction mixture prior to the addition of the zinc chloride stock. Mixing rates that result in product foaming will likely result in product aggregation and should be avoided. In one embodiment, the PEG is mPEG. In one embodiment, the activated PEG is PEG-O-2-methylpropionaldehyde. In another embodiment, the activated mPEG is mPEG-O-2-methylpropionaldehyde. In one embodiment, the PEG has a molecular weight of about 20 kDa.

In one embodiment, the Lewis acid catalyst is added to the mixture of mixture of activated PEG and IFN β in a second step to provide a mixture of activated PEG, IFN β and Lewis acid catalyst. In another embodiment, the Lewis acid catalyst is a zinc cation. In one embodiment, the amount of Lewis acid catalyst added to the activated PEG and IFN β mixture is sufficient to provide a concentration of Lewis acid catalyst in a PEG coupling reaction mixture from about 0.78 mM to about 1.2 mM. In another embodiment, the amount of Lewis acid catalyst added to the activated PEG and IFN β mixture is sufficient to provide a concentration of zinc chloride in a PEG coupling reaction mixture from about 0.9 mM to about 1.1 mM. In a further embodiment, the amount of Lewis acid catalyst added to the activated PEG and IFN β mixture is sufficient to provide a concentration of Lewis acid catalyst in a PEG coupling reaction mixture from about 0.95 mM to about 1.05 mM. In an additional embodiment, the amount of Lewis acid catalyst added to the activated PEG and IFN β mixture is sufficient to provide a concentration of Lewis acid catalyst in a PEG coupling reaction mixture of about 1.0 mM. When adding a Lewis acid catalyst stock solution to the activated PEG and IFN β mixture, care should be taken to ensure that the volume of the Lewis acid catalyst stock solution that is added is only that necessary in order to ensure that the remaining reagents in the PEG coupling reaction will all reach the required levels. The rate of mixing is not critical for the Lewis acid catalyst addition step; however, adequate mixing should preferably be achieved over a 14-16 minute period. Mixing rates that result in product foaming which can result in product aggregation and should be avoided.

In a third step, $NaCNBH_3$ is added to the mixture of activated PEG, IFN β and optional Lewis acid catalyst to form a PEG coupling reaction mixture. In one embodiment, the amount of $NaCNBH_3$ added to the activated PEG, IFN β and optional Lewis acid catalyst mixture is sufficient to provide a concentration of $NaCNBH_3$ in a PEG coupling reaction mixture from about 15 mM to about 25 mM. In another embodiment, the amount of $NaCNBH_3$ added to the activated PEG, IFN β and optional Lewis acid catalyst mixture is sufficient to provide a concentration of $NaCNBH_3$ in a PEG coupling reaction mixture from about 18 mM to about 22 mM. In a further embodiment, the amount of $NaCNBH_3$ added to the activated PEG, IFN β and optional Lewis acid catalyst mixture is sufficient to provide a concentration of $NaCNBH_3$ in a PEG coupling reaction mixture of about 20 mM. The $NaCNBH_3$ is added to the activated PEG, IFN β and optional Lewis acid catalyst with stirring. In one embodiment, the $NaCNBH_3$ is added over a period of time from about 45 min to about 240 min. In another embodiment, the $NaCNBH_3$ is added over a period of time from about 45 min to about 80 min. In a further embodiment, the $NaCNBH_3$ is added over a period of time of about 60 min. When adding a $NaCNBH_3$ stock solution to the activated PEG, IFN β and optional Lewis acid catalyst mixture, care should be taken to ensure that the volume of the $NaCNBH_3$ stock solution that is added is only that necessary in order to ensure that the remaining reagents in the PEG coupling reaction will all reach the required levels. The initial agitation (14-16 min) of the reaction mixture is preferred to ensure proper mixing and a uniform concentration of $NaCNBH_3$ throughout the reaction vessel; unmixed reactions can lead to incomplete mono-PEG IFN conversion.

In a fourth step, the PEG coupling reaction mixture is incubated to produce mono-mPEG IFN β. In one embodiment, the incubation is performed for about 5 hours to about 9 hours. In another embodiment, the incubation is performed for about 7 hours to about 9 hours. In a further embodiment, the incubation is performed for about 8 hours to about 8.5 hours. In an additional embodiment, the incubation is performed for about 8.5 hours.

In order to reduce degradation of the materials and products, to reduce dissolved oxygen and to dilute the HCN and $H_2$ gases produced during the reaction, it is preferred to employ an inert gas overlay in the reaction vessel. In one embodiment, it is preferred to use an inert gas overlay rate of 3-5 LPM for (a) heating the purified IFN β solution in the reaction vessel, (b) adding the activated PEG to the reaction vessel and (c) adding the optional Lewis acid catalyst to the reaction vessel. In another embodiment, it is preferred to use an inert gas overlay rate of 10 LPM for (a) adding the $NaCNBH_3$ to the reaction vessel, (b) incubating the PEG coupling reaction mixture and (c) quenching the PEC coupling reaction. The inert gas overlay rate is increased to 10 LPM in order to decrease the dissolved oxygen in the reaction vessel, but also to dilute the HCN and $H_2$ gases produced during the reaction. Reduced inert gas overlay rates may lead to increased dissolved oxygen (potential product dimerization/aggregation), as well as increased measured levels of HCN and $H_2$ (possible buildup of toxic gas in the vessel), but because the PEGylation reaction is carried out in a closed system, this will have little effect on the process operators. In one embodiment, the inert gas is argon. In another embodiment, the inert gas is nitrogen.

Although not a critical parameter for the PEG coupling reagent, the hold time of the quenched PEG coupling reaction mixture is critical for maximizing the amount of purified mono-PEG IFN β recovered from the PEG coupling reaction mixture. The quenched PEG coupling reaction mixture can be held for up to 48 hours at about 2° C. to about 25° C. before initiating purification of the mono-PEG IFN β. In one embodiment, the hold temperature is about 18° C. to about 25° C., preferably about 20° C. to about 23° C. In another embodiment, the hold temperature is about 2° C. to about 8° C. In a further embodiment, the hold temperature is about 8° C. to about 18° C. The PEG IFN β is purified using conventional techniques. Thus, in one embodiment, the present invention also provides a PEG IFN β purified from the PEG coupling reaction or the quenched PEG coupling reaction obtained in accordance with the process of this embodiment.

In a second aspect, the present invention provides a PEG coupling reaction mixture. In one embodiment, the PEG coupling reaction mixture comprises the following elements:

(a) IFN β at a concentration from about 0.4 mg/ml to about 4.0 mg/ml;

(b) activated PEG at a molar ratio of activated PEG to IFN β from about 1:1 to about 20:1; and (c) $NaCNBH_3$ at a concentration from about 5 mM to about 100 mM, wherein the pH of the PEG reaction mixture is from about 4.0 to about 6.0.

In one embodiment, the PEG coupling reaction mixture further comprises a Lewis acid catalyst at a concentration from about 0.1 mM to about 2.2 mM. In another embodiment, the Lewis acid catalyst is a zinc cation. In a further embodiment, the PEG coupling reaction mixture further comprises arginine at a concentration in the reaction mixture from about 25 mM to about 250 mM. In one embodiment, the PEG coupling reaction mixture further comprising arginine is quenched. In a further embodiment, the PEG coupling reaction mixture in the reaction vessel is overlaid with an inert gas. In one embodiment, the inert gas is argon. In another embodiment, the inert gas is nitrogen. In one embodiment, the IFN β is IFN β-1a. In another embodiment, the IFN β is IFN β-1b. In one embodiment, the PEG is mPEG. In one embodiment, the activated PEG is PEG-O-2-methylpropionaldehyde. In another embodiment, the activated PEG is mPEG-O-2-methylpropionaldehyde. In one embodiment, the PEG has a molecular weight of about 20 kDa.

The PEG IFN β is purified using conventional techniques. Thus, in one embodiment, the present invention also provides a PEG IFN β purified from the PEG coupling reaction or the quenched PEG coupling reaction obtained in accordance with this embodiment.

In another embodiment, the PEG coupling reaction mixture comprises the following elements:
(a) IFN β at a concentration from about 1.5 mg/ml to about 2.8 mg/ml, preferably from about 2.0 mg/ml to about 2.8 mg/ml, more preferably from about 2.5 mg/ml to about 2.8 mg/ml, more preferably about 2.8 mg/ml;
(b) activated PEG at a molar ratio of activated PEG to IFN β from about 1:1 to about 5:1, preferably from about 1.5:1 to about 5:1, more preferably from about 1.5:1 to about 2:1, still more preferably about 1.5:1; and
(c) NaCNBH$_3$ at a concentration from about 15 mM to about 25 mM, preferably from about 18 mM to about 22 mM, more preferably about 20 mM, wherein the pH of the PEG coupling reaction mixture is from about 4.8 to about 5.2, preferably from about 4.9 to about 5.1, more preferably about 5.0.

In one embodiment, the PEG coupling reaction further comprises a Lewis acid catalyst at a concentration from about 0.78 mM to about 1.2 mM, preferably from about 0.9 mM to about 1.1 mM, more preferably from about 0.95 mM to about 1.05 mM, still more preferably about 1.0 mM. In another embodiment, the Lewis acid catalyst is a zinc cation.

In a further embodiment, the PEG coupling reaction mixture further comprises arginine at a concentration in the reaction mixture from about 50 mM to about 150 mM, preferably from about 75 mM to about 125 mM, more preferably about 100 mM. In one embodiment, the PEG coupling reaction mixture further comprising arginine is quenched. In another embodiment, the PEG coupling reaction mixture is in a reaction vessel. In a further embodiment, the PEG coupling reaction mixture in the reaction vessel is overlaid with an inert gas. In one embodiment, the inert gas is argon. In another embodiment, the inert gas is nitrogen.

In one embodiment, the IFN β is IFN β-1a. In another embodiment, the IFN β is IFN β-1b. In one embodiment, the PEG is mPEG. In one embodiment, the activated PEG is PEG-O-2-methylpropionaldehyde. In another embodiment, the activated PEG is mPEG-O-2-methylpropionaldehyde. In one embodiment, the PEG has a molecular weight of about 20 kDa.

The PEG IFN β is purified using conventional techniques. Thus, in one embodiment, the present invention also provides a PEG IFN β purified from the PEG coupling reaction or the quenched PEG coupling reaction obtained in accordance with this embodiment.

The PEG IFN β in the PEG coupling reaction mixture or in the quenched PEG coupling reaction is purified using conventional techniques well known to the skilled artisan. Such purification techniques may include use of a SP-Sepharose chromatography column and a Superose 6 HR 10/30 FLPC sizing column. Alternatively, a purification technique may include a fractogel EMD SE HiCap cation exchange column. Ultrafiltration/diafiltration can be used to concentrate the purified mono-PEG IFN β. The purified-mono-PEG IFN β is formulated for use and stored at −70° C. in Teflon bottles. Thus, in one embodiment, the present invention provides a mono-PEG IFN β purified from the PEG coupling reaction or the quenched PEG coupling reaction obtained in accordance with the present invention or from the PEG coupling reaction or the quenched PEG coupling reaction of the present invention. In one embodiment, the IFN β is IFN β-1a. In another embodiment, the IFN β is IFN β-1b. In a further embodiment, the PEG is mPEG. In another embodiment, the mPEG is 20 kDa mPEG.

The PEGylated interferons produced by the present invention can be formulated into pharmaceutical compositions using techniques well known to the skilled artisan. The PEG IFN β (also sometimes referred to as PEG IFN β conjugate or conjugate) of the present invention is administered in a pharmacologically-effective amount to treat any of the conditions described above, and is based on the IFN β activity of the conjugate. The term "pharmacologically-effective amount" means the amount of a drug or pharmaceutical agent that will elicit the biological or medical response of a tissue, system, animal or human that is being sought by a researcher or clinician. It is an amount that is sufficient to significantly affect a positive clinical response while maintaining diminished levels of side effects. The amount of PGC IFN-beta which may be administered to a subject in need thereof is in the range of 0.01-100 µg/kg, or more preferably 0.01-10 µ/kg, administered in single or divided doses.

Administration of the described dosages may be every other day, but preferably occurs once a week or once every other week. Doses are typically administered over at least a 24 week period by injection.

Administration of the dose can be oral, topical, intravenous, subcutaneous, intramuscular, or any other acceptable systemic method. Based on the judgment of the attending clinician, the amount of drug administered and the treatment regimen used will, of course, be dependent on the age, sex and medical history of the patient being treated, the neutrophil count (e.g., the severity of the neutropenia), the severity of the specific disease condition and the tolerance of the patient to the treatment as evidenced by local toxicity and by systemic side-effects.

In practice, the conjugates of the invention are administered in amounts which will be sufficient to inhibit or prevent undesired medical conditions or disease in a subject, such as a mammal, and are used in the form most suitable for such purposes. The compositions are preferably suitable for internal use and include an effective amount of a pharmacologically-active compound of the invention, alone or in combination with other active agents, with one or more pharmaceutically-acceptable carriers. The compounds are especially useful in that they have very low, if any, toxicity.

The conjugates herein described can form the active ingredient of a pharmaceutical composition, and are typically administered in a mixture with suitable pharmaceutical diluents, excipients or carriers (collectively referred to herein as "carrier" materials) suitably selected with respect to the intended form of administration, that is, oral tablets, capsules, elixirs, syrups and the like. The compositions typically will include an effective amount of active compound or the pharmaceutically-acceptable salt thereof, and in addition, and may also include any carrier materials as are customarily used in the pharmaceutical sciences. Depending on the intended mode of administration, the compositions may be in solid, semi-solid or liquid dosage form, such as, for example, injectables, tablets, suppositories, pills, time-release capsules, powders, liquids, suspensions, or the like, preferably in unit dosages.

Conventional pharmaceutical compositions comprising a pharmacologically-effective amount of a conjugate, e.g., PEG IFN β, together with pharmaceutically-acceptable carriers, adjuvants, diluents, preservatives and/or solubilizers may be used in the practice of the invention. Pharmaceutical compositions of interferon include diluents of various buffers (e.g., arginine, Tris-HCl, acetate, phosphate) having a range of pH and ionic strength, carriers (e.g., human serum albumin), solubilizers (e.g., tween, polysorbate), and preservatives (e.g., benzyl alcohol). See, for example, U.S. Pat. No. 4,496,537.

Administration of the active compounds described herein can be via any of the accepted modes of administration for therapeutic agents. These methods include systemic or local administration such as oral, nasal, parenteral, transdermal, subcutaneous, or topical administration modes.

For instance, for oral administration in the form of a tablet or capsule (e.g., a gelatin capsule), the active drug component can be combined with an oral, non-toxic pharmaceutically-acceptable inert carrier such as ethanol, glycerol, water, and the like. Moreover, when desired or necessary, suitable binders, lubricants, disintegrating agents, and coloring agents can also be incorporated into the mixture. Suitable binders include starch, magnesium aluminum silicate, starch paste, gelatin, methylcellulose, sodium carboxymethylcellulose and/or polyvinylpyrrolidone, sugars, corn sweeteners, natural and synthetic gums such as acacia, tragacanth or sodium alginate, polyethylene glycol, waxes and the like. Lubricants used in these dosage forms include sodium oleate, sodium stearate, magnesium stearate, sodium benzoate, sodium acetate, sodium chloride, silica, talcum, stearic acid, its magnesium or calcium salt, and/or polyethylene glycol and the like. Disintegrators include, without limitation, starch, methyl cellulose, agar, bentonite, xanthan gum starches, agar, alginic acid or its sodium salt, or effervescent mixtures, and the like. Diluents, include, e.g., lactose, dextrose, sucrose, mannitol, sorbitol, cellulose and/or glycine. The conjugates of the invention can also be administered in such oral dosage forms as timed-release and sustained-release tablets or capsules, pills, powders, granules, elixers, tinctures, suspensions, syrups, and emulsions. Liquid, particularly injectable compositions can, for example, be prepared by dissolving, dispersing, etc. The active compound is dissolved in or mixed with a pharmaceutically-pure solvent such as, for example, water, saline, aqueous dextrose, glycerol, ethanol, and the like, to thereby form the injectable solution or suspension. Additionally, solid forms suitable for dissolving in liquid prior to injection can be formulated. Injectable compositions are preferably aqueous isotonic solutions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically-valuable substances.

The conjugates of the present invention can be administered in intravenous (e.g., bolus or infusion), intraperitoneal, subcutaneous or intramuscular form, all using forms well known to those of ordinary skill in the pharmaceutical arts. Injectables can be prepared in conventional forms, either as liquid solutions or suspensions.

Parental injectable administration is generally used for subcutaneous, intramuscular or intravenous injections and infusions. For example, when a subcutaneous injection is used to deliver 0.01-100 µg/kg, or more preferably 0.01-10 µg/kg of PEGylated IFN-beta over one week, two injections of 0.005-50 µg/kg, or more preferably 0.005-5 µg/kg, respectively, may be administered at 0 and 72 hours. Additionally, one approach for parenteral administration employs the implantation of a slow-release or sustained-released system, which assures that a constant level of dosage is maintained, according to U.S. Pat. No. 3,710,795.

Furthermore, preferred conjugates for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen. Other preferred topical preparations include creams, ointments, lotions, aerosols, sprays and gels, wherein the amount administered would be 10-100 times the dose typically given by parenteral administration.

For solid compositions, excipients include pharmaceutical grades of mannitol, lactose, starch, magnesium stearate, sodium saccharin, talcum, cellulose, glucose, sucrose, magnesium carbonate, and the like may be used. The active compound defined above, may be also formulated as suppositories using for example, polyalkylene glycols, for example, propylene glycol, as the carrier. In some embodiments, suppositories are advantageously prepared from fatty emulsions or suspensions.

The conjugates of the present invention can also be administered in the form of liposome delivery systems, such as small unilamellar vesicles, large unilamellar vesicles and multilamellar vesicles. Liposomes can be formed from a variety of phospholipids, containing cholesterol, stearylamine, or phosphatidylcholines. In some embodiments, a film of lipid components is hydrated with an aqueous solution of drug to a form lipid layer encapsulating the drug, as described in U.S. Pat. No. 5,262,564.

Conjugates of the present invention may also be delivered by the use of immunoglobulin fusions as individual carriers to which the compound molecules are coupled. The compounds of the present invention may also be coupled with soluble polymers as targetable drug carriers. Such polymers can include polyvinylpyrrolidone, pyran copolymer, polyhydroxypropyl-methacrylamide-phenol, polyhydroxyethyl-aspanamidephenol, or polyethyleneoxidepolylysine substituted with palmitoyl residues. The conjugates can also be coupled to proteins, such as, for example, receptor proteins and albumin. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

If desired, the pharmaceutical composition to be administered may also contain minor amounts of non-toxic auxiliary substances such as wetting or emulsifying agents, pH buffering agents, and other substances such as for example, sodium acetate, triethanolamine oleate, etc.

The dosage regimen utilizing the conjugates is selected in accordance with a variety of factors including type, species, age, weight, sex and medical condition of the patient; the severity of the condition to be treated; the route of administration; the renal and hepatic function of the patient; and the particular compound or salt thereof employed. The activity of the compounds of the invention and sensitivity of the patient to side effects are also considered. An ordinarily skilled physician or veterinarian can readily determine and prescribe the effective amount of the drug required to prevent, counter or arrest the progress of the condition.

Oral dosages of the present invention, when used for the indicated effects, will range between about 0.01-100 µg/kg/day orally, or more preferably 0.01-10 µg/kg/day orally. The compositions are preferably provided in the form of scored tablets containing 0.5-5000 µg or more preferably 0.5-500 µg of active ingredient.

For any route of administration, divided or single doses may be used. For example, compounds of the present invention may be administered daily or weekly, in a single dose, or the total dosage may be administered in divided doses of two, three or four.

Any of the above pharmaceutical compositions may contain 0.1-99%, 1-70%, or, preferably, 1-50% of the active compounds of the invention as active ingredients.

As described above, the course of the disease and its response to drug treatments may be followed by clinical examination and laboratory findings. The effectiveness of the therapy of the invention is determined by the extent to which the previously described signs and symptoms of a condition, e.g., chronic hepatitis, are alleviated and the extent to which the normal side effects of interferon (i.e., flu-like symptoms such as fever, headache, chills, myalgia, fatigue, etc. and central nervous system related symptoms such as depression, paresthesia, impaired concentration, etc.) are eliminated or substantially reduced.

The PEGylated interferons can be used for the treatment of conditions that are susceptible to treatment with interferon which are well known to the skilled artisan using accepted modes of administration. See, for example, U.S. Pat. No. 8,017,733 which describes pharmaceutical compositions, administration and treatments using PEGylated interferons. Such conditions include, but are not limited to, cell proliferation disorders, in particular multiple sclerosis, cancer (e.g., hairy cell leukemia, Kaposi's sarcoma, chronic myelogenous leukemia, multiple myeloma, basal cell carcinoma and malignant melanoma, ovarian cancer, cutaneous T cell lymphoma), viral infections or disease, chronic hepatitis C. Viral infections include, but are not limited to, hepatitis A, hepatitis B, hepatitis C, other non-A/non-B hepatitis, herpes virus, Epstein-Barr virus (EBV), cytomegalovirus (CMV), herpes simplex, human herpes virus type 6 (HHV-6), papilloma, poxvirus, picomavirus, adenovirus, rhinovirus, human T lymphotropic virus-type 1 and 2 (HTLV-1/-2), human rotavirus, rabies, retroviruses including human immunodeficiency virus (HIV), encephalitis, and respiratory viral infections. For example, the PEG IFN purified from the PEG coupling reaction mixture is used to treat multiple sclerosis, particularly relapsing-remitting multiple sclerosis (RRMS). RRMS is characterized by clearly defined attacks of worsening neurologic function. These attacks—often called relapses, flare-ups or exacerbations—are followed by partial or complete recovery periods (remissions), during which symptoms improve partially or completely, and there is no apparent progression of disease. RRMS is the most common disease course at the time of diagnosis. Approximately 85 percent of people are initially diagnosed with RRMS, compared to 10-15 percent with progressive forms of the disease.

A phase 3 Efficacy and Safety Study of PEG IFN β-1a for treating RRMS has been conducted. See Calabresi et al., 2014, *Lancel Neurol* 13(7):657-665, incorporated herein by reference. In this study, investigators worldwide randomly assigned 1512 people with relapsing MS to one of three groups: placebo, PEG IFN β-1a 125 µg delivered subcutaneously (under the skin) every two weeks, or PEG IFN β-1a 125 µg delivered subcutaneously every four weeks. The primary objective of the study was to determine the effects of the drug versus placebo on the annualized relapse rate after 48 weeks. Secondary objectives included the effects on central nervous system damage as observed on MRI scans, and disease progression as measured by the EDSS disability scale. After the first year, participants on placebo were re-assigned to receive PEG IFN β-1a every two or four weeks, and those already on therapy remained in their respective groups.

Results for the first year of the study showed that the annualized relapse rate was reduced significantly more than placebo, by 35.6% in the two-week dosing group, and by 27.5% in the four-week dosing group. New lesions (areas of tissue damage) on MRI scans were reduced by 67% in the two-week dosing group and by 28% in the four-week dosing group. The risk of disability progression (confirmed over 12 weeks), as measured by the EDSS scale, was reduced by 38% in both PEG IFN β-1a groups.]

Thus in one embodiment for the treatment of RRMS, PEG IFN β-1a is dosed once every 2 weeks and is administered subcutaneously with an autoinjector or a prefilled syringe. A recommended dose of PEG IFN β-1a is 125 µg every 14 days. It is recommended that patients should start treatment with 63 µg on day 1. On day 15, the dose is increased to 94 µg, reaching the full dose of 125 µg on day 29.

EXAMPLES

The present invention is described by reference to the following Examples, which is offered by way of illustration and is not intended to limit the invention in any manner Standard techniques well known in the art or the techniques specifically described below were utilized.

Example 1

PEGylation Reaction

Purified, recombinantly produced IFN β-1a in an ultrafiltration pool is transferred to a closed, jacketed stainless steel reaction vessel and the temperature is brought to 18° C.-26° C. under constant mixing. The target volume is 21 L-22.5 L. A stock solution of 20 kDa mPEG-O-2-methyl-propionaldehyde in acetate, Bis-Tris buffer is prepared and added to the IFN β-1a to a target concentration of 4.5 mg/mL active 20 kDa mPEGO-2-methylpropionaldehyde. The target pH of the coupling reaction is pH 5. At pH 5, the reductive amination chemistry occurs selectively at the α-amino group of the N-terminal amino acid residue because it is significantly less protonated than the α-amino group of lysine residues. Following mixing, a stock solution of the Lewis acid catalyst is added to the reaction mixture to a target concentration of 1 mM. The mild reductant NaCNBH₃ is then added as a stock solution (under constant mixing) to the reaction mixture to a final concentration of 20 mM over a period of 1 hr. Reduction with NaCNBH₃ results in a stable covalent C—N bond between the 20 kDa mPEG-O-2-methylpropionaldehyde and the protein. An argon, overlay is applied during the coupling procedure to sweep out any hydrogen and hydrogen cyanide gas that may evolve. The reaction mixture is incubated for 5-9 hours followed by the addition of a stock arginine solution to a final concentration of 100 mM. The excess arginine quenches the reaction by reacting with the remaining active 20 kDa mPEG-O-2-methylpropionaldehyde to form a 20 kDa mPEG-O-2-methylpropionylarginine, which is later removed by SE HiCap cation exchange chromatography. The quenched reaction pool is held for up to 48 hours prior to further processing.

Example 2

PEGylation Reaction

Example 1 is repeated except that the ultrafiltration pool was stored frozen before running the PEG coupling reaction. The bottles are thawed at ambient temperature, pooled into the same reaction vessel and brought to ambient temperature.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed, as well as any fraction therein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It will be appreciated that the methods and compositions of the instant invention can be incorporated in the form of a variety of embodiments, only a few of which are disclosed herein. Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A process for coupling PEG to IFN β comprising the following steps:
   (a) adding activated PEG to a purified IFN β solution in a reaction vessel to form a mixture of activated PEG and IFN β, wherein the purified IFN β solution has a concentration of IFN β from about 1.75 mg/ml to about 3.3 mg/ml and a temperature of from about 2° C. to about 30° C., wherein the amount of activated PEG added is sufficient to provide a molar ratio of activated PEG to IFN β in a PEG coupling reaction mixture from about 1:1 to about 20:1 and wherein the pH of the mixture is from about 4.0 to about 6.0;
   (b) optionally adding a Lewis acid catalyst to the mixture, wherein the amount of Lewis acid catalyst when added is sufficient to provide a concentration of Lewis acid catalyst in the PEG coupling reaction mixture from about 0.1 mM to about 2.2 mM;
   (c) adding NaCNBH$_3$ to the mixture to form the PEG coupling reaction mixture with stirring over a period of about 5 minutes to about 600 minutes, wherein the amount of NaCNBH$_3$ added is sufficient to provide a concentration of NaCNBH$_3$ in the PEG coupling reaction mixture from about 15 mM to about 25 mM; and
   (d) incubating the PEG coupling reaction mixture for about 10 minutes to about 9 hours to produce preferentially mono-PEG IFN β,
   wherein the PEG is mPEG-O-2-methylpropionaldehyde.

2. The process of claim 1, wherein a Lewis acid catalyst is added to the reaction mixture.

3. The process of claim 2, wherein the Lewis acid catalyst is a zinc cation.

4. The process of claim 1, further comprising quenching the PEG coupling reaction to stop the reaction.

5. The process of claim 4, wherein the PEG coupling reaction is quenched by adding arginine.

6. The process of claim 5, wherein the amount of arginine in the quenched reaction mixture is from about 25 mM to about 250 mM.

7. The process of claim 4, wherein the mixture in the quenching step is overlaid with an inert gas.

8. The process of claim 7, wherein the inert gas overlay rate is 10 LPM.

9. The process of claim 4, wherein the quenched PEG coupling reaction is held for up to 48 hours at about 2° C. to about 30° C. before purifying the mono-PEG IFN β.

10. The process of claim 1, wherein the IFN β is IFN β-1a.

11. The process of claim 1, wherein the IFN β is brought to said temperature before being added to the reaction vessel.

12. The process of claim 1, wherein the IFN β is added to the reaction vessel and then brought to said temperature.

13. The process of claim 1, wherein the mixtures in steps (a)-(d) are overlaid with an inert gas.

14. The process of claim 13, wherein the inert gas overlay rate is 3-5 liter per minute (LPM) for steps (a) and (b) and is 10 LPM for steps (c) and (d).

15. A process for coupling PEG to IFN β comprising the following steps:
   (a) adding activated PEG to a purified IFN β solution in a reaction vessel to form a mixture of activated PEG and IFN β, wherein the purified IFN β solution has a concentration of IFN β from about 1.75 mg/ml to about 3.3 mg/ml and a temperature of from about 19° C. to about 27° C. and wherein the amount of activated PEG added is sufficient to provide a molar ratio of activated PEG to IFN β in a PEG coupling reaction mixture from about 1:1 to about 5:1 and wherein the pH of the mixture is from about 4.8 to about 5.2;
   (b) optionally adding a Lewis acid catalyst to the mixture, wherein the amount of Lewis acid catalyst when added is sufficient to provide a concentration of Lewis acid catalyst in the PEG coupling reaction mixture from about 0.78 mM to about 1.2 mM;
   (c) adding NaCNBH$_3$ to the mixture to form the PEG coupling reaction mixture with stirring over a period of about 45 minutes to about 240 minutes, wherein the amount of NaCNBH$_3$ added is sufficient to provide a concentration of NaCNBH$_3$ in the PEG coupling reaction mixture from about 15 mM to about 25 mM; and
(d) incubating the PEG coupling reaction mixture for about 5 hours to about 9 hours to produce preferentially mono-PEG IFN β,
wherein the PEG is mPEG-O-2-methylpropionaldehyde.

16. The process of claim 15, wherein the Lewis acid catalyst is added to the reaction mixture.

17. The process of claim 16, wherein the Lewis acid catalyst is a zinc cation.

18. The process of claim 17, wherein the zinc cation concentration in the PEG coupling reaction is from about 0.9 mM to about 1.1 mM, preferably from about 0.95 mM to about 1.05 mM, more preferably about 1.0 mM.

19. The process of claim 15, further comprising quenching the PEG coupling reaction to stop the reaction.

20. The process of claim 19, wherein the PEG coupling reaction is quenched by adding arginine.

21. The process of claim 20, wherein the amount of arginine in the quenched reaction mixture is from about 50 mM to about 150 mM, preferably from about 75 mM to about 125 mM, more preferably about 100 mM.

22. The process of claim 19, wherein the quenched PEG coupling reaction is held for up to 48 hours at about 2° C. to about 25° C. before purifying the mono-PEG IFN β.

23. The process of claim 15, wherein the IFN β is IFN β-1a.

24. The process of claim 15, wherein the IFN β is brought to said temperature before being added to the reaction vessel.

25. The process of claim 15, wherein the IFN β is added to the reaction vessel and then brought to said temperature.

26. The process of claim 15, wherein the IFN β concentration in the purified IFN β solution is from about 2.4 mg/ml to about 3.3 mg/ml, preferably about 2.9 mg/ml to about 3.3 mg/ml, more preferably about 3.3 mg/ml.

27. The process of claim 15, wherein the molar ratio of activated PEG to IFN β in the PEG coupling reaction mixture is from about 1.5:1 to about 5:1, preferably from about 1.5:1 to about 2:1, more preferably about 1.5:1.

28. The process of claim 15, wherein the NaCNBH$_3$ concentration in the PEG coupling reaction is from about 18 mM to about 22 mM, preferably about 20 mM.

29. The process of claim 15, wherein the molar ratio of activated PEG to IFN β in the PEG coupling reaction mixture is from about 1.5:1 to about 5:1, preferably from about 1.5:1 to about 2:1, more preferably about 1.5:1.

30. The process of claim 15, wherein the temperature is from about 21° C. to about 25° C., preferably from about 22° C. to about 24° C., more preferably about 23° C.

31. The process of claim 15, wherein the pH is from about 4.9 to about 5.1, preferably about 5.0.

32. The process of claim 15, wherein the mixtures in steps (a)-(d) are overlaid with an inert gas.

33. The process of claim 32, wherein the inert gas overlay rate is 3-5 LPM for steps (a) and (b) and is 10 LPM for steps (c) and (d).

34. The process of claim 15, wherein the pH is 5.0, the temperature is 23° C., the IFN β concentration in the purified IFN β solution is 3.3 mg/ml, the molar ratio of activated PEG to IFN β is about 1.5:1 and the NaCNBH$_3$ concentration in the PEG coupling reaction is about 20 mM.

35. The process of claim 34, wherein the Lewis catalyst is a zinc cation at a concentration in the PEG coupling reaction of about 1.0 mM.

36. The process of claim 34, wherein the PEG coupling reaction is quenched by adding arginine to the PEG coupling reaction mixture to a concentration of 100 mM in the quenched reaction mixture.

37. The process of claim 34, wherein the mixtures in steps (a)-(d) are overlaid with an inert gas at an inert gas overlay rate of 3-5 LPM for steps (a) and (b) and of 10 LPM for steps (c) and (d).

* * * * *